United States Patent [19]

Uchino et al.

[11] 4,363,755
[45] Dec. 14, 1982

[54] LIQUID ALPHA-OLEFIN SULFONATE SHAMPOO COMPOSITION WITH INCREASED LOW TEMPERATURE STABILITY

[75] Inventors: Noriyuki Uchino; Tōru Ōno, both of Tokyo, Japan

[73] Assignee: The Lion Corporation, Tokyo, Japan

[21] Appl. No.: 251,123

[22] Filed: Apr. 6, 1981

[30] Foreign Application Priority Data

Apr. 15, 1980 [JP] Japan .................................. 55/49460

[51] Int. Cl.$^3$ .......................... C11D 1/84; C11D 1/34
[52] U.S. Cl. ............................... 252/545; 252/174.16; 252/554; 252/555; 252/DIG. 13; 252/DIG. 14
[58] Field of Search .................. 252/174.16, 545, 554, 252/555, DIG. 13, DIG. 17, DIG. 14

[56] References Cited

U.S. PATENT DOCUMENTS

| | | | |
|---|---|---|---|
| 4,070,309 | 1/1978 | Jacobsen | 252/547 |
| 4,132,679 | 1/1979 | Tsutsumi et al. | 252/545 |
| 4,139,485 | 2/1979 | Imokawa et al. | 252/135 |
| 4,259,204 | 3/1981 | Homma | 252/174.16 |

FOREIGN PATENT DOCUMENTS

| | | | |
|---|---|---|---|
| 2341592 | 2/1975 | Fed. Rep. of Germany | 252/545 |
| 54-134712 | 10/1979 | Japan | 252/545 |
| 55-29563 | 3/1980 | Japan | 252/545 |

*Primary Examiner*—P. E. Willis, Jr.
*Attorney, Agent, or Firm*—Schwartz, Jeffery, Schwaab, Mack, Blumenthal & Koch

[57] ABSTRACT

A liquid shampoo composition having both superior stability at low temperatures and a conditioning property, which contains (a) an anionic surface active agent (I) represented by the general formula:

OS—M (wherein OS is an acid residue of a straight-chained olefin sulfonate having an average carbon number of 10 to 16, and M is an alkali- or alkaline earth metal)

in an amount of 3 to 30% by weight of the composition weight; (b) at least one member selected from the group consisting of an anionic surface active agent (II) represented by the general formula:

PS—N (wherein PS is an acid residue of a branched alkyl sulfonate having an average carbon number of 10 to 18, and M is an alkali- or alkaline earth metal)

and an ampholytic surface active agent represented by the general formula:

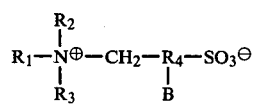

(wherein $R_1$ is a straight-chained or branched alkyl radical having an average carbon number of 10 to 18, both $R_2$ and $R_3$ are independently alkyl radicals having a carbon number of 1 to 3, $R_4$ is an alkylene radical having a carbon number of 1 to 3, and B is H or OH radical)

in an amount of 1 to 15% by weight of the composition weight; and (c) a phosphoric ester represented by the general formula:

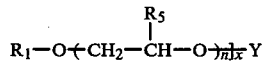

(wherein $R_1$ is a straight-chained or branched alkyl radical having an average carbon number of 10 to 18; $R_5$ is H or an alkyl radical having a carbon number of 1 or 2; n is an integer of 5 to 15; and x is 1 when

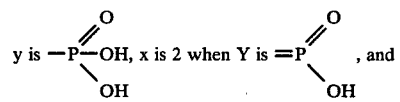

in an amount of 0.3 to 7% by weight of the composition weight.

7 Claims, No Drawings

LIQUID ALPHA-OLEFIN SULFONATE SHAMPOO COMPOSITION WITH INCREASED LOW TEMPERATURE STABILITY

BACKGROUND OF THE INVENTION

The present invention relates to an improvement in a liquid shampoo composition containing an α-olefin sulfonate as a major component.

Heretofore, there have been employed various anionic surface active agents and nonionic surface active agents as surface active agents constituting liquid shampoo compositions. Of these, anionic surface active agents in the form of a sodium salt or an ethanolamine salt have frequently been employed. Among the anionic surface active agents, an α-olefin sulfonate possesses high foaming ability and detergency. The α-olefin sulfonate, however, has a drawback, unlike an alkyl ethoxy sulfate and the like, in that it causes white turbidity at low temperatures because it has inferior stability at low temperatures. For this reason, application of the α-olefin sulfonate to liquid detergents has been difficult because of its poor commercial value, although the α-olefin sulfonate possesses superior performance.

Generally, an α-olefin sulfonate is a mixture containing a hydroxyalkane monosulfonate, an alkene monosulfonate and a small amount of an alkene disulfonate. Each of these components further contains several types of structural isomers. The mixture is recognized as an "α-olefin sulfonate" in the detergent industry. Since each of the components of the α-olefin sulfonate has a different crystallization point, the α-olefin sulfonate causes white turbidity where the component having the highest crystallization point is first allowed to precipitate as crystals at low temperatures. Once it causes white turbidity, the α-olefin sulfonate is unlikely to be easily returned again to a transparent state.

In order to improve the stability of the α-olefin sulfonate at low temperatures, it may be considered that a known hydrotrope (a compound possessing the ability to increase the water-solubility of an organic compound) such as ethanol, propylene glycol, glycerin or the like be added. In this case, the effect of depressing the freezing point of water can be recognized. However, not only the effect of improving the stability at low temperatures of the -olefin sulfonate can be little improved, but the free water in the α-olefin sulfonate is decreased, thereby causing an increase in the amount of crystals precipitated at low temperatures.

As examples of employing an α-olefin sulfonate demonstrating such defects as hereinabove mentioned as a liquid detergent, British Pat. No. 1,225,218 illustrates examples obtained by adding alkali metal salts, ammonium salts or organic base salts of an alkyl- or alkenyl polyglycol ether carboxylic acid to an α-olefin sulfonate having 8 to 20 carbon atoms; and U.S. Pat. No. 3,852,221 illustrates examples prepared by adding a substituted fatty acid amido component and a sulfonated hydrotrope component and the like to an α-olefin sulfonate. In the detergents illustrated in these publications, however, the stabilities at low temperatures of the α-olefin sulfonates are not improved to a sufficient extent.

With a sense of consumer demand, a liquid shampoo composition has been desired with a function of favorably maintaining conditions after hair washing (smoothness, lack of stickiness and the like) or a conditioning property in combination with the above functions which should be naturally present in shampoos.

Accordingly, it has become important to produce liquid shampoo compositions that have superior conditioning properties and good stability at low temperatures; for example, at −5° C. or lower in winter in accordance with storage conditions.

SUMMARY OF THE INVENTION

The object of the present invention is to provide a liquid shampoo composition possessing superior stability at low temperatures and a conditioning property.

In accordance with the present invention, there is provided a liquid shampoo composition containing:

(a) an anionic surface active agent (I) represented gy the general formula:

$$OS-M$$

(wherein OS is an acid residue of a straight-chained olefin sulfonate having an average carbon number of 10 to 16, and M is an alkali- or alkaline earth metal) in an amount of 3 to 30% by weight of the composition weight;

(b) at least one member selected from the group consisting of an anionic surface active agent (II) represented by the general formula:

$$PS-M$$

(wherein PS is an acid residue of a branched alkyl sulfonate having an average carbon number of 10 to 18, and M is an alkali- or alkaline earth metal) and an ampholytic surface active agent represented by the general formula:

$$R_1-\overset{\overset{R_2}{|}}{\underset{\underset{R_3}{|}}{N^\oplus}}-CH_2-R_4-SO_3^\ominus$$
$$\phantom{R_1-N^\oplus-CH_2-R_4}\phantom{-}B$$

(wherein $R_1$ is a straight-chained or branched alkyl radical having an average carbon number of 10 to 18, both $R_2$ and $R_3$ are independently alkyl radicals having an average carbon number of 1 to 3, $R_4$ is an alkylene radical having a carbon number of 1 to 3, and B is H or OH radical) in an amount of 1 to 15% by weight of the composition weight; and (c) a phosphoric ester represented by the general formula:

$$[R_1-O(CH_2-\overset{\overset{R_5}{|}}{C}H-O)_{\overline{n}}]_x Y$$

(wherein $R_1$ is a straight-chained or branched alkyl radical having an average carbon number of 10 to 18; $R_5$ is H or an alkyl radical having a carbon number of 1 or 2; n is an integer of 5 to 15; and x is 1 when $$Y \text{ is } -\overset{\overset{O}{\|}}{\underset{\underset{OH}{\backslash}}{P}}-OH, \quad x \text{ is } 2 \text{ when } Y \text{ is } =\overset{\overset{O}{\|}}{\underset{\underset{OH}{\backslash}}{P}}, \text{ and}$$

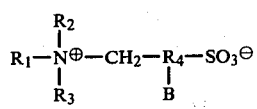

in an amount of 0.3 to 7% by weight of the composition weight.

DETAILED DESCRIPTION OF THE PREFERRED EMBODIMENTS

The liquid shampoo composition in accordance with the present invention contains at least three essential components.

The first essential component of the liquid shampoo composition in accordance with the present invention is an anionic surface active agent represented by the general formula:

OS—M (wherein OS is an acid residue of a straight-chained olefin sulfonate having an average carbon number of 10 to 16, and M is an alkali- or alkaline earth metal). The first essential component is a substance generally called an "α-olefin sulfonate". The α-olefin sulfonate may be prepared by forming a thin film of α-olefin having an average carbon number of 10 to 16 and obtainable, for example, by the wax cracking process or the ethylene polymerization process using a Ziegler catalyst; converting the -olefin into the corresponding sulfonate with a gaseous sulfuric acid anhydride diluted with an inert gas; neutralizing the sulfonate with an alkali metal salt or an alkaline earth metal salt, such as sodium hydroxide; and subjecting the product to hydrolysis. The product thus prepared is a mixture containing 10 to 45% by weight of HOS (Hydroxyalkane Sulfonate) (provided that the HOS comprises a dihydroxy compound contained in an amount of 0.5 to 8% by weight, usually 1 to 5% by weight, and a polyhydroxy compound including a trihydroxy- and other polyhydroxy compounds contained in an amount of 5 to 44.5% by weight); 55 to 80% by weight of ANS (Alkenyl Sulfonate); and 3 to 15% by weight of DS (Alkenyl Disulfonate).

The amount of anionic surface active agent mentioned hereinabove ranges from 3 to 30% by weight and, preferably, from 7 to 20% by weight of the weight of the liquid shampoo composition.

The second essential component of the liquid shampoo composition in accordance with the present invention is an anionic surface active agent represented by the general formula:

PS—M (wherein PS is an acid residue of a branched alkyl sulfonate having an average carbon number of 10 to 18, and M is an alkali- or alkaline earth metal) and/or an an ampholytic surface active agent represented by the general formula:

$$R_1-\overset{R_2}{\underset{\underset{B}{|}}{\overset{|}{N^\oplus}}}-CH_2-R_4-SO_3^\ominus$$

(wherein $R_1$ is a straight-chained or branched alkyl radical having an average carbon number of 10 to 18, both $R_2$ and $R_3$ are independently alkyl radicals having a carbon number of 1 to 3, $R_4$ is an alkylene radical having a carbon number of 1 to 3, and B is H or OH radical).

The second essential component can improve the stability of the liquid shampoo composition at low temperatures.

The anionic surface active agent constituting the second essential component is a paraffin sulfonate which, in turn, may be prepared by a process for adding an acidic sulfite to a monoolefin, a process for reacting an inorganic sulfite with an alkyl halide, sulfochlorination or sulfoxidation of paraffin, and the like. The paraffin sulfonate, as the second essential component, has an average carbon number of 10 to 18, preferably 12 to 16. The preferred paraffin sulfonate is one having a $C_{10}$-$C_{18}$ straight-chained or branched alkyl radical and having the sulfonic radical bonded to the inner carbon of the alkyl radical.

The ampholytic surface active agent constituting the second essential component of the liquid shampoo composition in accordance with the present invention is a sulfobetaine represented by the above-mentioned general formula. The sulfobetaine is usually prepared by reacting an excessive amount of a long chain alkyl dimethylamine with a halohydroxyalkane sulfonate in a reaction medium consisting of an alcohol or a mixture of an alcohol with water.

The amount of the paraffin sulfonate and the sulfobetaine to be added singly or in a mixture thereof may range from 1 to 15% by weight and, preferably, from 2 to 10% by weight of the liquid shampoo composition. When the amount thereof is not greater than 1% by weight, the stability at low temperatures of the shampoo composition is not improved, while when the amount exceeds 15% by weight, the stability of the shampoo composition at low temperatures is also not improved either, because the free water in the composition is presumably decreased.

The third essential component of the liquid shampoo composition in accordance with the present invention is a phosphoric ester represented by the general formula:

$$[R_1-O+CH_2-\overset{R_5}{\underset{|}{CH}}-O\cdot]_{\overline{n}x}Y$$

(wherein $R_1$ is a straight-chained or branched alkyl radical having an average carbon number of 10 to 18; $R_5$ is H or an alkyl radical having a carbon number of 1 or 2; n is an integer of 5 to 15; and x is 1 when

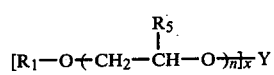

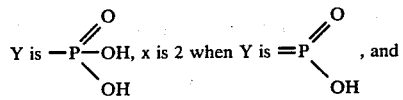

The phosphoric ester, as represented hereinabove, when used in a mixture with the above-mentioned first and second essential components, can improve the stability at low temperatures and provide the shampoo with a conditioning property.

It is not desirable to use a phosphoric ester having an alkyl radical $R_1$ with a carbon number of less than 10, because it decreases the surface activity of the shampoo composition. It is also undesirable to use a phosphoric ester having an alkyl radical $R_1$ with a carbon number of more than 18, because the stability at low temperatures and the conditioning property of the shampoo composition are not improved to a sufficient extent. It is undesirable when n is less than 5 because the stability at low temperatures and the conditioning property of the shampoo composition are not improved. It is also undesirable when n exceeds 15, because the conditioning property is inferior. The most preferable n value is in the range of 7 to 12.

The amount of the phosphoric ester to be added may range from 0.3 to 7% by weight, and preferably from 0.5 to 5% by weight of the shampoo composition. When the amount thereof does not reach 0.3% by weight, it is undesirable because the stability at low temperatures and the conditioning property are inferior. It is also undesirable to use the phosphoric ester in an amount exceeding 7% by weight because stickiness results after washing and rinsing the hair.

The liquid shampoo composition in accordance with the present invention contains water as a solvent. It may also contain an alcohol miscible with water, such as ethanol or the like.

The liquid shampoo composition in accordance with the present invention may further contain various other additives as long as they do not impair the objects of the present invention. The amounts of these additives, however, should be small.

As hereinabove set forth, the liquid shampoo composition in accordance with the present invention is not only superior in the detergency required for liquid shampoo compositions, but it also improves to a large extent the stability at low temperatures and the conditioning property, which are inferior in conventional shampoo compositions. The liquid shampoo composition according to the present invention can meet the demands of both consumers and the barber and beauty parlor industries.

The present invention will now be described in more detail by way of examples in contrast to comparative examples. Methods of evaluating the performance of the liquid shampoo compositions of the examples and comparative examples are carried out in the following ways:

Stability at Low Temperatures

A specimen is placed in a transparent bottle which in turn is stored in a constant temperature bath having a constant temperature of −5° C. Visual observation is then made on the appearance of the specimen, and the stability at low temperatures is evaluated according to the number of days required for precipitation of materials as follows:
A: No precipitation occured in 31 days or more.
B: Precipitation occured in 14 to 30 days.
C: Precipitation occured in 13 days or less.
Conditioning Property An overall evaluation is made with respect to three performance characteristics: coefficient of static friction, smoothness of hair after washing, and absence of stickiness after rinsing. Each of the performance characteristics is measured by the following methods:

(1) Coefficient of Static Friction

A 20-cm strand of hair (5 g) is washed with 1.0 g of a shampoo composition sample by being rubbed for 1 minute, rinsed, and dried by placing the hair in a constant temperature bath at a constant temperature of 25° C. and a relative humidity of 65% for 24 hours. The hair specimen is then measured for its coefficient of static friction with a friction meter (manufactured by Shinko Electric Co., Ltd.). It is noted that superior smoothness of hair according to organoleptic examination is perceivable when the coefficient of static friction is 0.17 or lower as supported by the organoleptic examination to be described below.

(2) Smoothness of Hair

Evaluation is made by organoleptic examination. In the same manner as with the measurement for the coefficient of static friction, a 20-cm strand hair (5 g) is washed, rinsed and dried. The hair of 20 test subjects is washed using SDS (Sodium Dodecyl Sulfate) as a shampoo, and the smoothness of the hair specimen is compared with that of the hair washed with SDS.

Evaluation is rated as follows:
Rating:
++: Superior in smoothness to the hair washed with SDS
+: Slightly superior in smoothness to the hair washed with SDS
±: Equal in smoothness to the hair washed with SDS (3) Absence of Stickiness of Hair After Rinsing Evaluation is made by organoleptic examination. The hair of a test subject is parted in the middle, and the parted hair is washed on one side with 3.0 g of a specimen shampoo and on the other side with 3.0 g of a control shampoo (a commercially available shampoo). After rinsing, the degree of stickiness of the hair is examined and rated as follows:
Rating:

++: Not sticky when compared with the hair washed with the commercially available shampoo
+: Slightly sticky when compared with the hair washed with the commercially available shampoo
±: More sticky than the hair washed with the commercially available shampoo

EXAMPLES 1-5

The shampoo compositions in accordance with the present invention, with varying amounts of PS-Na as the second component, were evaluated for their performance and were rated. The results are shown in Table 1. In these examples and in the examples below, amounts to be added are expressed as % by weight. The term "AOS-Na" in the table means sodium salt of an α-olefin sulfonate.

TABLE 1

| | Comparative Example 1 | Example 1 | Example 2 | Example 3 | Example 4 | Example 5 | Comparative Example 2 |
|---|---|---|---|---|---|---|---|
| Component | | | | | | | |
| $C_{14}AOS$—Na | 10 | 10 | 10 | 10 | 10 | 10 | 10 |

TABLE 1-continued

|  | Comparative Example 1 | Example 1 | Example 2 | Example 3 | Example 4 | Example 5 | Comparative Example 2 |
|---|---|---|---|---|---|---|---|
| PS-Na*[1] | 0.5 | 1 | 3 | 5 | 10 | 15 | 20 |
| Phosphoric*[2] ester | 3 | 3 | 3 | 3 | 3 | 3 | 3 |
| Ethanol | 3 | 3 | 3 | 3 | 3 | 3 | 3 |
| Distilled water | balance | balance | balance | balance | balance | balance | balance |
| Performance | | | | | | | |
| Stability at Low Temperature ($-5°$ C.) | C | A | A | A | A | A | B |
| Coefficient of Static Friction | 0.17 | 0.17 | 0.17 | 0.17 | 0.17 | 0.17 | 0.17 |
| Smoothness of Hair | ++ | ++ | ++ | ++ | ++ | ++ | ++ |
| Absence of Stickiness after Rinsing | ++ | ++ | ++ | ++ | ++ | ++ | ++ |

*[1]Sodium $C_{14}$-$C_{18}$ paraffin sulfonate; Hostapur SAS-93 (Hoechst A.G., Germany)
*[2]Lauryl alcohol EO 10 moles, phosphoric ester, $R_1 = C_{12}H_{25}$, $R_5 = H$, $n = 10$, $Y$ = mono/di/tri = 59/40/1

EXAMPLES 6-10

The shampoo compositions in accordance with the present invention, with varying amounts of sulfobetaine as the second component, were measured for their performance. The results are shown in Table 2.

TABLE 2

|  | Comparative Example 3 | Example 6 | Example 7 | Example 8 | Example 9 | Example 10 | Comparative Example 4 |
|---|---|---|---|---|---|---|---|
| Component | | | | | | | |
| $C_{14}$AOS—Na | 10 | 10 | 10 | 10 | 10 | 10 | 10 |
| Sulfobetain*[3] | 0.5 | 1 | 3 | 5 | 10 | 15 | 20 |
| Phosphoric*[4] ester | 3 | 3 | 3 | 3 | 3 | 3 | 3 |
| Ethanol | 3 | 3 | 3 | 3 | 3 | 3 | 3 |
| Distilled water | balance | balance | balance | balance | balance | balance | balance |
| Performance | | | | | | | |
| Stability at Low Temperature ($-5°$ C.) | C | A | A | A | A | A | B |
| Coefficient of Static Friction | 0.17 | 0.17 | 0.17 | 0.17 | 0.17 | 0.17 | 0.17 |
| Smoothness of Hair | ++ | ++ | ++ | ++ | ++ | ++ | ++ |
| Absence of Stickiness during Rinsing | ++ | ++ | ++ | ++ | ++ | ++ | ++ |

*[3]
$$C_{12}H_{25}-\overset{\overset{CH_3}{|}}{\underset{\underset{CH_3}{|}}{N^{\oplus}}}-CH_2\overset{\overset{}{}}{\underset{\underset{OH}{|}}{CH}}CH_2SO_3^{\ominus}$$

*[4]Same as in *[2].

EXAMPLE 11-13

The shampoo compositions in accordance with the present invention, with varying amounts of phosphoric ester as the third component, were measured for their performance. The results are shown in Table 3.

TABLE 3

|  | Comparative Example 5 | Example 11 | Example 12 | Example 13 | Comparative Example 6 |
|---|---|---|---|---|---|
| Component | | | | | |
| $C_{14}$AOS—Na | 10 | 10 | 10 | 10 | 10 |
| PS-Na*[5] | 3 | 3 | 3 | 3 | 3 |
| Phosphoric*[6] ester | 0 | 0.3 | 1 | 7 | 9 |
| Ethanol | 3 | 3 | 3 | 3 | 3 |
| Distilled water | balance | balance | balance | balance | balance |
| Performance | | | | | |
| Stability at Low Temperature ($-5°$ C.) | B | A | A | A | A |
| Coefficient of Static Friction | 0.20 | 0.17 | 0.17 | 0.17 | 0.17 |
| Smoothness of Hair | ± | ++ | ++ | ++ | ++ |
| Absence of | | | | | |

TABLE 3-continued

| | Comparative Example 5 | Example 11 | Example 12 | Example 13 | Comparative Example 6 |
|---|---|---|---|---|---|
| Stickiness during Rinsing | ++ | ++ | ++ | ++ | ± |

*5Same as in *1.
*6Same as in *2.

EXAMPLES 14–17

The shampoo compositions in accordance with the present invention, with varying amounts of EO added to the phosphoric ester as the third component, were measured for their performance. The results are shown in Table 4.

TABLE 4

| | Comparative Example 7 | Example 14 | Example 15 | Comparative Example 8 | Comparative Example 9 | Example 16 | Example 17 | Comparative Example 10 |
|---|---|---|---|---|---|---|---|---|
| Component | | | | | | | | |
| $C_{14}AOS$—Na | 10 | 10 | 10 | 10 | 10 | 10 | 10 | 10 |
| Ps-Na*7 | 3 | 3 | 3 | 3 | 0 | 0 | 0 | 0 |
| Sulfobetaine*8 | 0 | 0 | 0 | 0 | 3 | 3 | 3 | 3 |
| Phosphoric*9 ester | 0.5 | 0.5 | 0.5 | 0.5 | 0.5 | 0.5 | 0.5 | 0.5 |
| EO added to phosphoric ester, moles | 3 | 5 | 15 | 20 | 3 | 5 | 15 | 20 |
| Ethanol | 3 | 3 | 3 | 3 | 3 | 3 | 3 | 3 |
| Distilled water | balance | balance | balance | balance | balance | balance | balance | balance |
| Performance | | | | | | | | |
| Stability at Low Temperature (−5° C.) | B | A | A | A | B | A | A | A |
| Coefficient of Static Friction | 0.18 | 0.17 | 0.17 | 0.18 | 0.18 | 0.17 | 0.17 | 0.18 |
| Smoothness of Hair | +  | ++ | ++ | + | + | ++ | ++ | + |
| Absence of Stickiness during Rinsing | ++ | ++ | ++ | ++ | ++ | ++ | ++ | ++ |

*7Same as in *1.
*8Same as in *3.
*9Phosphoric acid esterified with $P_2O_5$ by adding EO to lauryl alcohol; $R_1 = C_{12}H_{25}$, $R_5 = H$, Y = mono/di/tri = 59/40/1

EXAMPLES 18 AND 19

The shampoo compositions in accordance with the present invention, using AOS-Na having varying carbon numbers as the first component, were measured for their performance. The results are shown in Table 5.

TABLE 5

| | Example 18 | Example 19 | Example 20 |
|---|---|---|---|
| Composition | | | |
| $C_{12-14}AOS$—Na | 15 | 0 | 15 |
| $C_{14-16}AOS$—Na | 0 | 15 | 0 |
| $C_{10-12}PS$—Na | 0 | 3 | 1.5 |
| Sulphobetaine*10 | 3 | 0 | 1.5 |
| Phosphoric ester*11 | 3 | 3 | 3 |
| Ethanol | 3 | 3 | 3 |
| Distilled water | balance | balance | balance |
| Performance | | | |
| Stability at Low Temperature (−5° C.) | A | A | A |
| Coefficient of Static Friction | 0.17 | 0.17 | 0.17 |
| Smoothness of Hair | ++ | ++ | ++ |
| Absence of Stickiness during Rinsing  | ++ | ++ | ++ |

*10
$$C_{16}H_{33}-\overset{\overset{CH_3}{|}}{\underset{\underset{CH_3}{|}}{N^{\oplus}}}-\underset{H}{CH_2CHCH_2SO_3^{\ominus}}$$

*11 $R_1 = C_{16}/C_{18} = 1/1$ (by weight)
$R_5 = CH_3$, n = 10
Y = mono/di = 6/4

It is apparent from the above-mentioned examples and comparative examples that shampoo compositions within the scope of the present invention are superior both in stability at low temperatures and in conditioning property, whereas shampoo compositions outside the scope of the present invention do not satisfy both requirements of stability at low temperatures and the conditioning property.

What we claim is:

1. A liquid shampoo composition comprising:
   (a) an anionic surface active agent (I) represented by the general formula:

OS—M (wherein OS is an acid residue or a straight-chained olefin sulfonate having an average carbon number of 10 to 16, and M is an alkali- or alkaline earth metal) in an amount of 3 to 30% by weight of the composition weight; said anionic surface active agent comprising alkenyl sulfonate, hydroxyalkane sulfonate and alkenyl disulfonate, said hydroxyalkane sulfonate containing dihydroxyalkane sulfonate;
   (b) at least one member selected from the group consisting of an anionic surface active agent (II) represented by the general formula:

PS—M (wherein PS is an acid residue of a branched alkyl sulfonate having an average carbon number of 10 to 18, and M is an alkali- or alkaline earth metal) and an ampholytic surface active agent represented by the general formula:

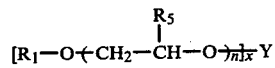

(wherein $R_1$ is a straight-chained or branched alkyl radical having an average carbon number of 10 to 18, both $R_2$ and $R_3$ are independent alkyl radicals with a carbon number of 1 to 3, $R_4$ is an alkylene radical having a carbon number of 1 to 3, and B is H or OH radical)
in an amount of 1 to 15% by weight of the composition weight; and
(c) a phosphoric ester represented by the general formula:

$$[R_1-O(CH_2-\overset{R_5}{\underset{|}{CH}}-O)_{\overline{n}}]_x Y$$

(wherein $R_1$ is a straight-chained or branched alkyl radical having an average carbon number of 10 to 18; $R_5$ is H or an alkyl radical having a carbon number of 1 or 2; n is an integer of 5 to 15; and x is 1 when

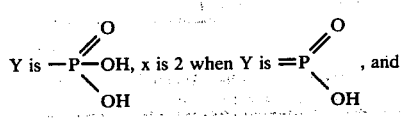

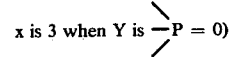

in an amount of 0.3 to 7% by weight of the composition weight.

2. A liquid shampoo composition according to claim 1, wherein the average carbon number of said anionic surface active agent (II) is 12 to 16.

3. A liquid shampoo composition according to claim 1, wherein said phosphoric ester is represented by the general formula wherein n is 7 to 12.

4. A liquid shampoo composition according to any one of claims 1 to 3, wherein the amount of said anionic surface active agent (I) is 7 to 20% by weight, the amount of said at least one member selected from the group consisting of said anionic surface active agent (II) and said ampholytic surface active agent is 2 to 10% by weight, and the amount of said phosphoric ester is 0.5 to 5% by weight.

5. A liquid shampoo composition according to claim 1, further containing water as a solvent.

6. A liquid shampoo composition according to claim 5, further containing an alcohol miscible with water.

7. A liquid shampoo composition according to claim 6, wherein said alcohol is ethanol.

* * * * *